United States Patent [19]

Denyer

[11] Patent Number: 5,687,912

[45] Date of Patent: Nov. 18, 1997

[54] ATOMIZER

[75] Inventor: J. Denyer, Pagham, United Kingdom

[73] Assignee: Medic-Aid Limited, West Sussex, England

[21] Appl. No.: 556,093

[22] Filed: Nov. 9, 1995

[30] Foreign Application Priority Data

Nov. 11, 1994 [GB] United Kingdom ............... 9422821

[51] Int. Cl.$^6$ ............................................. A61Z 11/02
[52] U.S. Cl. .................... 239/343; 239/338; 239/366; 128/200.21
[58] Field of Search ................... 239/343, 338, 239/370, 365, 366, 368, 371, 423, 424, 424.5, 433, 4; 128/200.18, 200.21, 200.22; 261/78.1, DIG. 65

[56] References Cited

U.S. PATENT DOCUMENTS

| 3,398,897 | 8/1968 | Urbanowicz | 239/358 |
| 3,516,771 | 6/1970 | Rendina | 239/338 X |
| 4,566,451 | 1/1986 | Badewien | 128/200.21 |
| 4,657,007 | 4/1987 | Carlin et al. | 128/200.21 |
| 5,533,497 | 7/1996 | Ryder | 128/200.21 |
| 5,533,501 | 7/1996 | Denyer | 128/200.21 |

FOREIGN PATENT DOCUMENTS

| 170715 | 2/1986 | European Pat. Off. |
| 627266 | 12/1994 | European Pat. Off. |
| 3429411 | 2/1986 | Germany |

*Primary Examiner*—Kevin Weldon
*Attorney, Agent, or Firm*—Nixon & Vanderhye P.C.

[57] ABSTRACT

An atomizer including a gas exit, an outlet adjacent the gas exit, and a deflector for deflecting gas issuing from the gas exit over the outlet for drawing a substance to be atomized out from one outlet and atomizing the substance in the gas issuing from the gas exit characterised in that the deflector is movable between a first position in the path of the gas issuing from the gas exit for atomization and a second and non-atomizing position.

25 Claims, 7 Drawing Sheets

ATOMIZER

BACKGROUND AND SUMMARY OF THE INVENTION

The present invention relates to atomizers and, in particular, to atomizers of the type which include a gas exit, at least one outlet in the region of the gas exit and a deflector for deflecting gas issuing from the gas exit across the at least one outlet whereby a substance to be atomized is drawn out of the at least one outlet and atomized. These atomizers atomize liquids or powders into the gas.

Most conventional atomizers of the above type operate continuously whether atomization is required or not. Strictly speaking, when such atomizers, frequently called nebulisers, are used in medical applications, atomization is only required during the inhalation phase of a breathing cycle so that a drug can be administered by deposition in the lungs. In practice a patient usually inhales for about 30 percent of the breathing cycle, consequently, use of a continuously operating atomizer results in a large proportion of the atomized drug being wasted.

Some designs of medical atomizer overcome such wastage by giving the patient a trigger to start the atomization when they begin to inhale. Such a trigger controlled type of atomizer is not satisfactory since the patient must coordinate inhalation with trigger operation.

In one conventional atomizer a gas duct leads gas under pressure to a gas exit, a reservoir for holding the substance to be atomized is formed around the base of the gas duct, and a sleeve placed around the gas duct defines a passageway through which the substance to be atomized may pass to at least one outlet. A fixed deflector in the form of a bar is disposed in line with the gas outlet so that gas issuing from the gas exit is deflected so as to pass over the outlet or outlets. The passage of gas over each outlet draws the substance to be atomised from the reservoir, through the passageway to each outlet. The deflected gas atomizes the substance, and atomized particles of the substance are carried away during the inhalation phase of the patient since the patient breathes air or gas in through the atomizer some of the drug is lost while the patient is not inhaling.

Atomizers are used in other applications. For example, powders or liquid may be sprayed from a jet, the liquid or powder being atomized and entrained by a propellant. In conventional sprays, operation is controlled by a valve for releasing propellant. When the valve is released, the spraying operation is stopped and some of the liquid or powder collects in the jet since insufficient propellant has been released. The collected spray either dries to block the jet or is propelled by a re-started spraying operation in large droplets. Where paint is being sprayed, this causes splatter and uneven deposition on a surface to be painted.

It is an object of this invention to reduce at least some of the above disadvantages of the above-mentioned prior art.

The present invention is defined in the appended claims.

BRIEF DESCRIPTION OF THE DRAWINGS

Embodiments of the invention are described below by way of example only with reference to the accompanying drawings in which:

FIG. 1 shows a first embodiment of the invention in a relaxed position;

FIG. 2 shows the first embodiment of the invention in a first operational position in which atomization takes place;

FIG. 3 shows the first embodiment of he invention in a second operational position in which atomization takes place;

FIG. 4 shows the first embodiment of the invention in a third operational position in which no atomization takes place;

FIGS. 5 and 6 show one embodiment of the flap valve and gas deflector;

FIG. 7 shows a second embodiment of the invention in a second operational position in which atomization takes place, FIG. 8 shows a further embodiment of the invention in which the movable baffle bar is located beneath the baffle, and FIG. 9 shows the further embodiment during inhalation by a patient.

DETAILED DESCRIPTION OF THE DRAWINGS

Referring to FIGS. 1 to 4, an atomizer includes a gas duct 6 which leads gas under pressure to a gas exit 4 within a jet head 3. The gas duct 6 passes through a wall of a reservoir 7 within which a substance to be atomised is held. A sleeve 8 is disposed around the jet head 3 and the gas duct 6. Passages are formed between the inner surface of the sleeve 8 and the outer surface of the gas duct 6 for leading the substance to be atomized from the reservoir 7 to outlets 5 in the jet head adjacent to the gas exit 4. For atomization of the substance to take place, a deflector 1 must be placed in the path of the pressurised gas exiting from the gas exit 4 so that it is redirected to pass directly over the outlets 5. This flow of pressure air draws the substance to be atomized from the reservoir 7, through the passage between the sleeve 8 and the gas duct 6 to the outlets 5. The flow of pressure air atomizes the substance as the substance leaves the outlets 5.

A downwardly and outwardly shaped baffle 9 is disposed around the jet head 3 to deflect the atomized substance downwards before it is carried away. It is important that the substance is atomized into very fine droplets. In medical applications, the substance to be atomized is a drug for administering to a patient by lung deposition. The finer the droplets, the deeper into the lungs the drug will pass. This maximises the deposition of the drug. Larger droplets collect on the inside of the baffle 9 where they coalesce to drop back down into the reservoir 7.

The atomizer also includes an air inlet 13 and an air outlet 14. In the above-mentioned medical application, as a patient inhales, ambient air is drawn into the atomizer through the inlet 13. The air then passes into the region of the air exit 4 and outlets 5 where droplets are entrained by the inhaled ambient air. The air then passes down under the baffle 9 before passing upwardly and out via the air outlet 14 carrying droplets of the drug to the patient. This action is described in more detail in British Patent application 9219327.5 and U.S. Pat. No. 5,533,501, which are hereby imported into this description in their entirety.

A planar arcuate gas deflector 1 is mounted above the gas exit to be movable about a pivot in that plane. The gas deflector 1 may be disposed across the gas exit 4, in which case atomization takes place, or may be disposed away from the gas exit 4, in which case no atomization takes place.

A vane 2 is joined to the deflector bar 1 so as to be pivotally mounted and to move with the deflector bar 1. The flap 2 responds to the breathing pattern of a patient by moving around the pivot.

When the apparatus is not in use, the vane assumes the position shown in FIG. 1 in which the gas deflector is not disposed across the gas exit. The vane forms a partial seal against a curved surface 12 (shown in outline). Even when pressure gas is issuing from the gas exit, no atomization takes place since the deflector is not disposed in the path of the gas.

Figure 2:
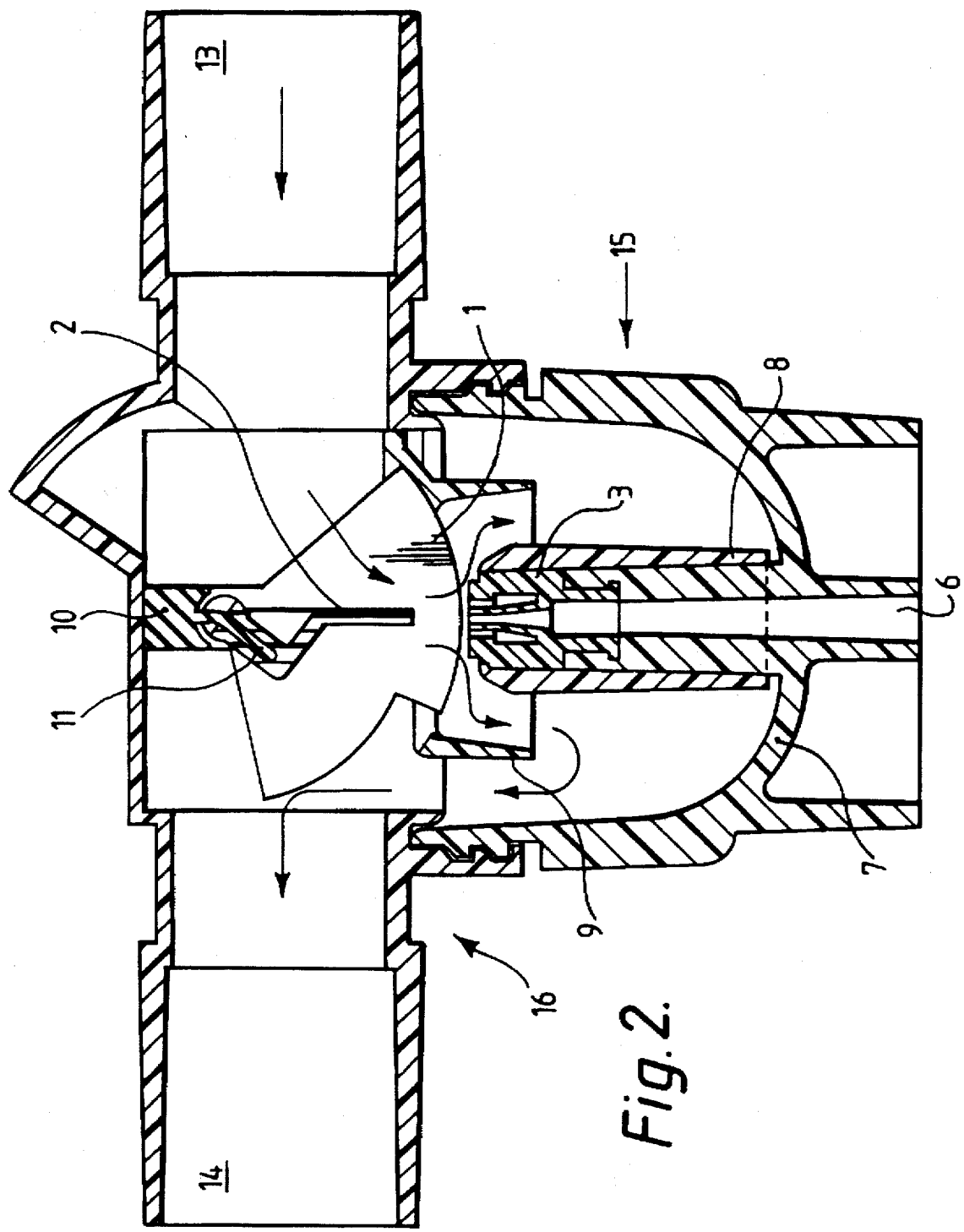

When a patient inhales, ambient air is drawn into the atomizer through the air inlet 13. The vane 2 is displaced into the position shown in FIG. 2 permitting and directing the ambient air to pass into the region of the gas exit before being directed downwardly and outwardly around the baffle. The air then escapes via the air outlet 14 to the patient. The displacement of the flap moves the deflector bar into the path of the gas issuing from the gas exit. Atomization therefore begins as soon as the patient begins to breath in. The atomized drug is carried away by the air passing through the atomizer. The vane must move only a few degrees before the deflector bar 1 is brought into position to commence atomization, but must move a few more degrees before breaking the seal between the flap and the curved surface to permit ambient air to enter the nebulizer. This ensures that the deflector is fully in position and atomizing cleanly before the ambient air passes through the atomizer to carry the droplets away.

The deflector extends further from the pivot than the flap so that the deflector can be positioned very close to the gas exit without obstruction from the flap. The curved surface 12 against which the vane seals therefore includes an arcuate slot through which the deflector may pass.

Figure 3:
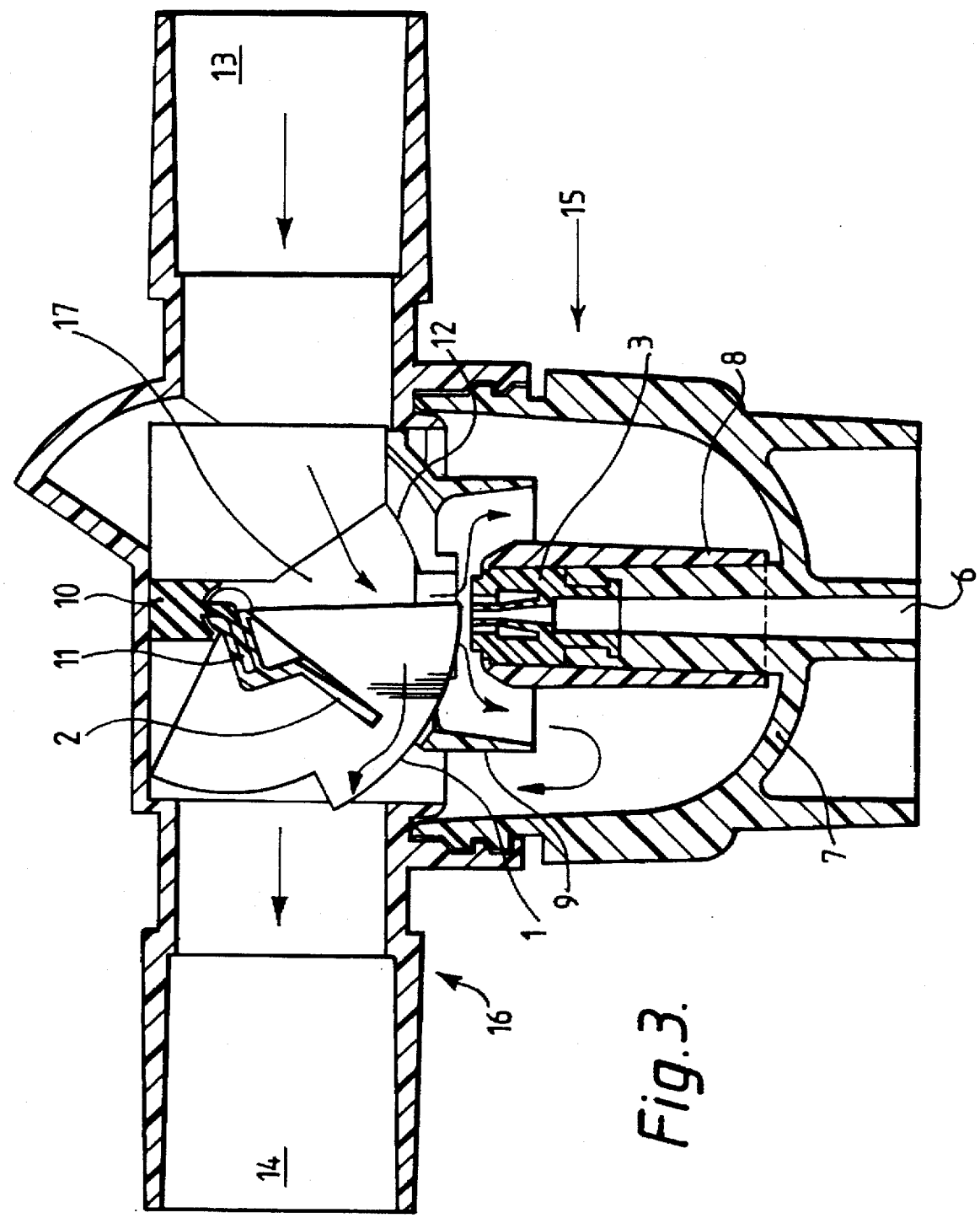

If the patient inhales sharply or quickly, the vane 2 assumes the position shown in FIG. 3 wherein the deflector bar 1 remains in the path of the gas exit so that atomization takes place, but excess air passes directly from the air inlet 13 to the air outlet 14 without entraining the atomized substance. The main reason for this is that the efficiency of entrainment of droplets decreases where air passes through the atomizer too quickly since a proportion of droplets will impact against the walls of the atomizer. A typical optimum flow rate is of the order of twenty five liters per minute.

Figure 4:
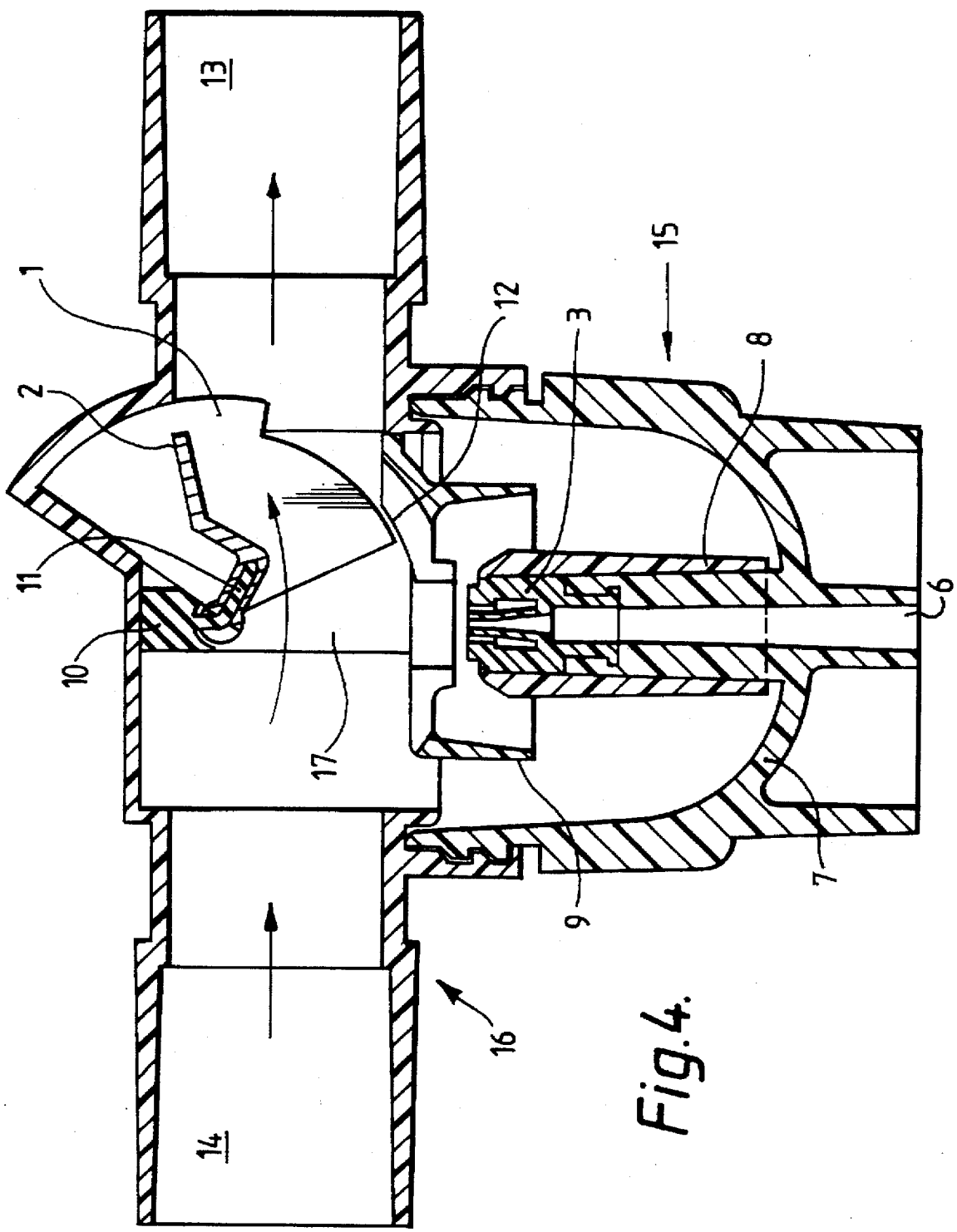

When the patient exhales, the vane 2 is displaced to a position as shown in FIG. 4 where the deflector is displaced such that it is not in the path of the gas exit. Atomization therefore does not occur, and so no drug is wasted. The vane allows exhaled air to pass directly from the air outlet 14 to the air inlet 13 without having to pass through the atomizing chamber. The combination of the vane 2 and the deflector 1 therefore constitutes a one-way valve.

Figure 1:
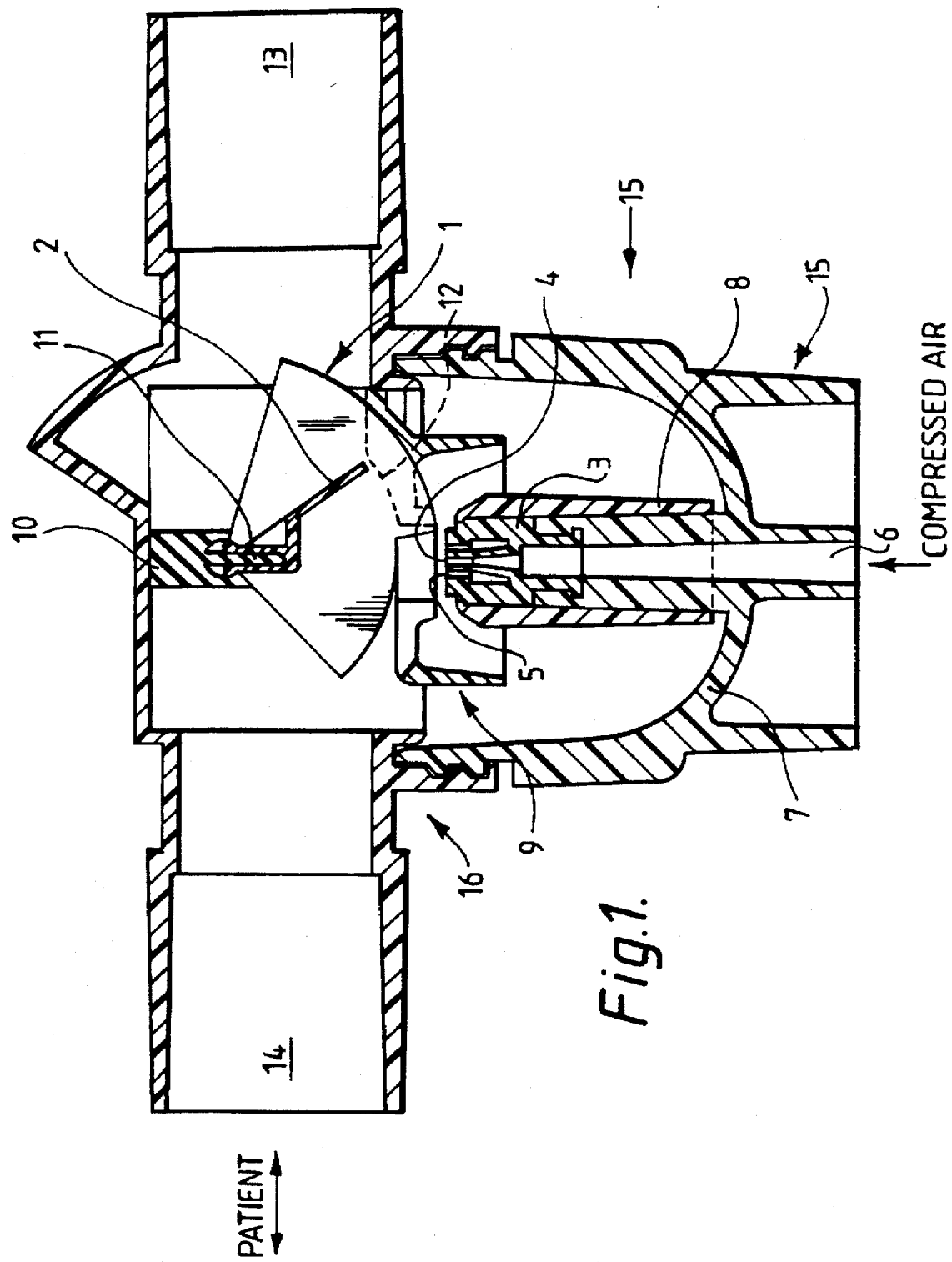

When the patient is not breathing in or out, the vane 2 is biassed towards the position shown in FIG. 1. The vane 2 and deflector 1 are mounted on a rubber tongue 11 extending from a fixed rubber block 10. The vane 2 and deflector 1 are therefore resiliently mounted.

The atomizer shown in FIGS. 1 to 4 includes three separable units. A base unit 15 includes the reservoir 7, the gas duct 6, the jet head 3 and outlets 5. The reservoir 7 includes a threaded rim. An upper unit 16 includes three air inlet 13, and the air outlet 14. The baffle 9, sleeve 8, frame members 17, the vane 2, gas deflector 1, the rubber tongue 11 and the fixed rubber block 10 constitute the third unit. Separation of the third unit permits the atomizer to be more easily cleaned. The vane 2 and gas deflector are connected to the air inlet 13 in the upper unit 16, and to the baffle 9 since the gas deflector 1 must pass through a slot in the baffle. The sleeve 8 may be part of the base unit 15, or part of the third unit.

Figure 5:
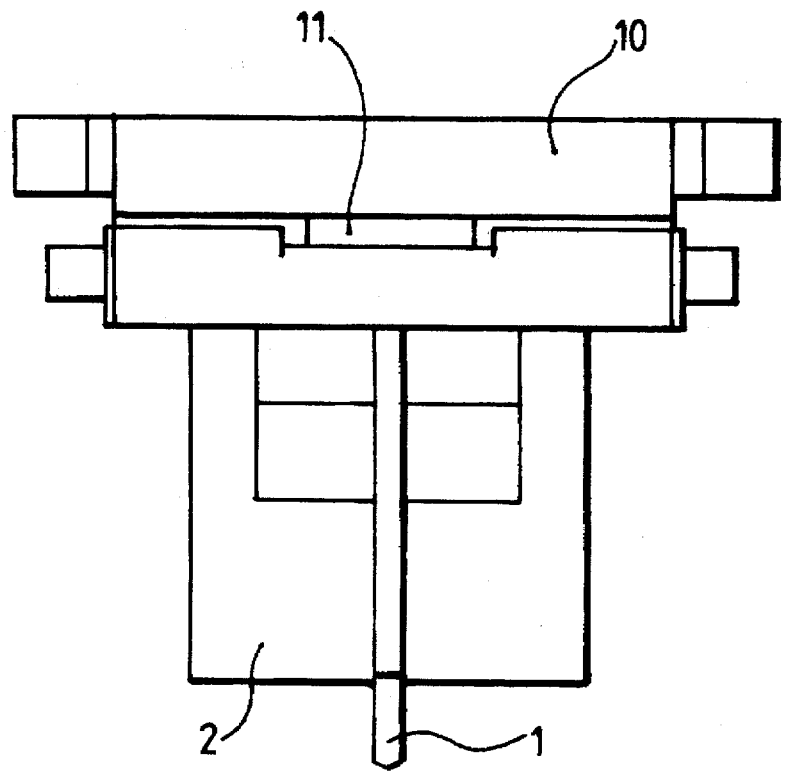
Figure 6:
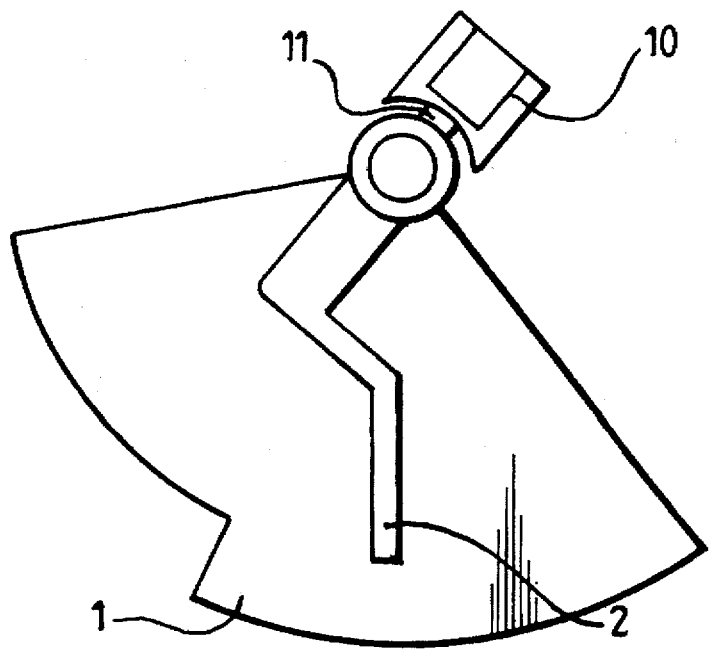

FIGS. 5 and 6 show the vane 2 and deflector 1 mounted on the fixed rubber block and rubber tongue. The rubber tongue 11 is held at the ends by the frame members 17 so that when the tongue 11 is bent by the vane, a load is applied. The vane 2 and deflector 1 are attached directly to the tongue 11 so that they are pivotally displaceable.

Figure 7:
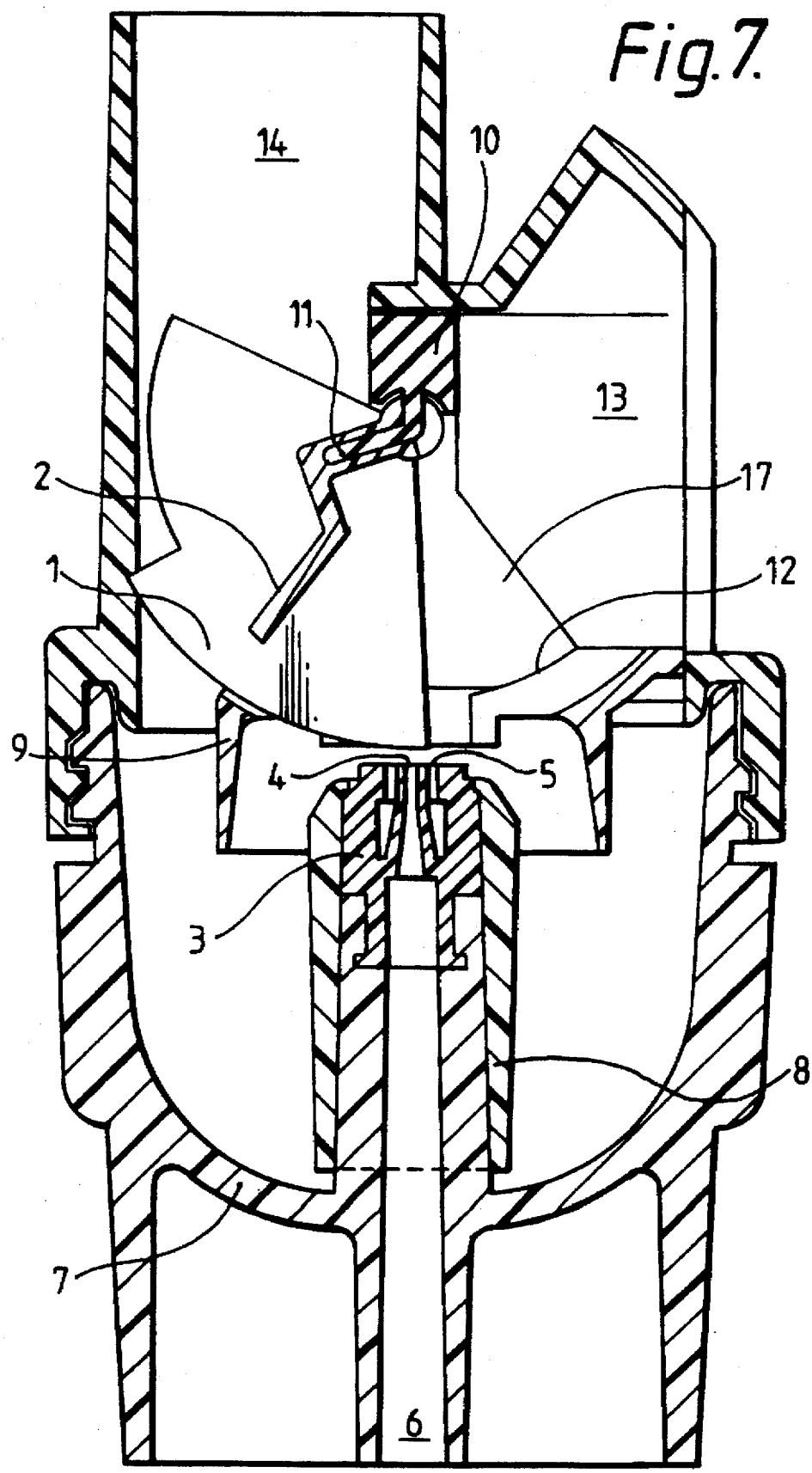

FIG. 7 shows a second embodiment of this invention in which the base unit 15 is exactly as described in relation to FIGS. 1 to 4. The vane 2 and deflector 1 are also mounted as described above. The main difference in this second embodiment is that the air outlet 14 leading to a patient extends vertically from the atomizer as shown in FIG. 7. Drug laden air does not have to pass around a sharp corner into the air outlet 14 once it has passed around the baffle 9. Fewer drug droplets will collect on the inner surface of the air outlet 14.

Referring to FIGS. 3, 4 and 7, the lower edge of the vane 2 forms a seal with the curved surface 12 as explained above. The vane 2 also includes two other edges which must be sealed. The vane 2 swings between two vertical wedge-shaped frame members 17 which form a seal so that flow of air to bypass the vane 2 is restricted when the vane 2 is disposed in any of the positions shown in FIGS. 1, 2 or 7. In the first and second embodiments shown in FIGS. 1 to 7, the frame members 17 also act as supports for the fixed rubber block 10. The frame members 17 may extend from the baffle 9, from the edge of the curved surface 12 or from the base unit 15. Where the frame members extend from the edge of the curved surface 12, the vane 2, deflector 1 and rubber block 10 are all mounted on the frame members 17 and within the upper unit 16.

According to another embodiment (not shown), the rubber block 10 is replaced by a metal spring eg. a leaf spring which permits the vane 2 and deflector 1 to be pivotally moveable in the same manner as described in relation to the rubber block 10 and tongue 11.

In a further embodiment (not shown) the vane 2 is omitted, and the deflector is movable into and out of the stream of gas issuing from the gas exit according to the breathing pattern of a patient. The vane is replaced by a flow sensor which detects when a patient begins to inhale and moves the deflector 1 into the path of gas issuing from the gas exit. In this embodiment the deflector is a bar which is moveable perpendicularly or laterally relevant to the longitudinal extent of the bar.

In another embodiment the deflector 1 is displaceable up and down in line with the gas issuing from the gas outlet. Once the deflector is raised above a certain height, atomization ceases to take place.

In yet a further embodiment, the deflector is not a straight bar, but is of any suitable shape for deflecting the gas across the outlets to cause atomization. The deflector may, for example, be a spherical ball disposed in the path of gas exiting the gas exit. The deflector may be a longitudinal blade movable into the path of the gas in the longitudinal direction of the blade.

In yet another embodiment (not shown) of this invention, the atomizer is used for producing a spray. This spray may be liquid droplets or powder particles. In medical applications, the spray may contain a drug. This spray producing apparatus may be used for producing sprays of paint droplets, perfume droplets or any other suitable liquids or powders. A base unit 15 of FIGS. 1–4 may be used to produce a gas exit 4 and outlets 5 for the substance to be atomized. A moveable deflector 1 is displaceable by a user. The user first activates a compressor which sends gas through the gas duct. For paint spraying, a mechanical compressor may be used, although this could be substituted for an aerosol propellant. The user then moves the deflector into the path of the gas issuing from the gas exit 4 to start atomization. The propellant then carries the droplets or powder through an outlet jet to form a spray. The user stops atomization before stopping the flow of gas from the gas exit. This keeps the outlet jet clean and free from paint and the like. A two-stage button can be used whereby atomization only takes place when the button is fully depressed while gas issues from the gas exit when the button is only partially depressed.

Figure 8:
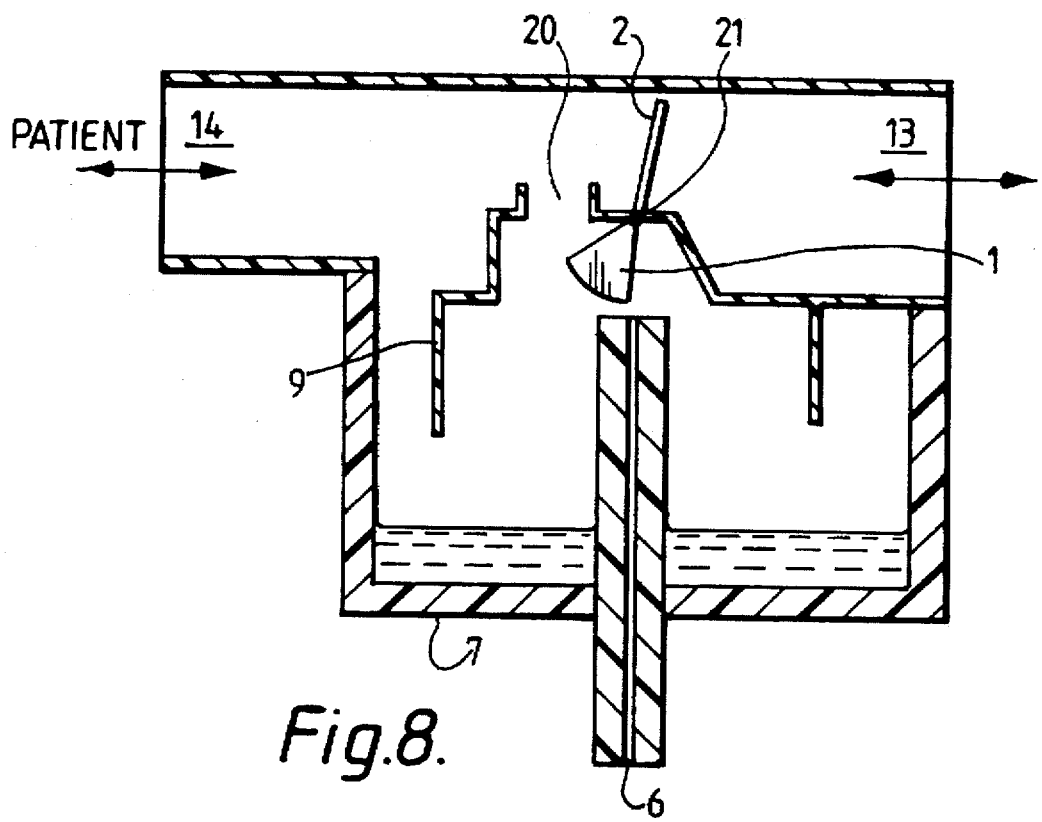
Figure 9:
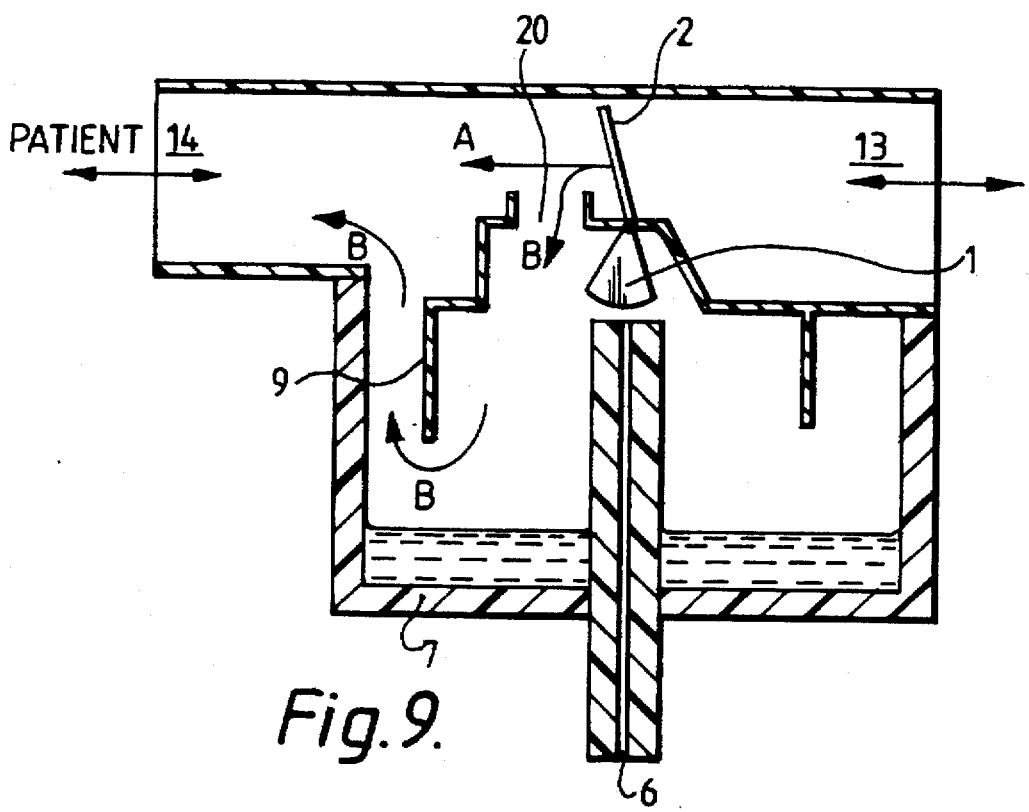

Under certain conditions, although 95% of the gas issuing from the gas exit 4 is deflected to either side of the deflector bar 1, a small amount hits the baffle bar depositing the substance to be atomized on the deflector bar 1. The gas which hits the baffle bar drives the liquid along the baffle bar towards the ends where the liquid can collect on top of the baffle 9 so that it is lost to the atomizer system. The whole dose of medicament is then not available to be administered to the patient. Furthermore, in some arrangements, as the deflector bar is moved out of the flow of gas issuing from the gas exit 4, the liquid that is running along the edge of the deflector bar 1 is sprayed into the top of the nebulizer where it collects without returning back to the reservoir 7. Referring now to FIGS. 8 and 9, the deflector bar 1 is housed entirely within the baffle 9 so that any liquid which collects on the deflector bar merely drips back into the reservoir, or if it is sprayed from the deflector bar by the flow of gas from the gas exit 4, is collected on the underside of the baffle 9 whereupon it coalesces and drops back down into the reservoir 7. FIG. 8 shows the nebulizer in a position where the patient is not inhaling. The segment shaped deflector bar 1 is disposed outside the line of gas exiting from the gas exit 4 so that nebulization does not take place. The segment is pivoted at a pivot point 21, and is also connected to the vane or flap 2. When a patient inhales, air is drawn into the nebulizer through air inlet 13, and deflects the vane or flap 2 moving the deflector bar 1 into line with the gas exit thus causing atomization of the substance to occur. For clarity, the outlets 5 and the sleeve 8 are not shown in the Figure. However the jet head is arranged in the same way as described in connection with FIGS. 1 to 7. The atomization of the substance causes the pressure beneath the baffle 9 to be decreased thereby drawing part of the inhaled air under the baffle 9 as shown by arrow B. The baffle 9 includes an aperture 20 for permitting the flow of air for entraining droplets B to enter beneath the baffle 9. A proportion of the inhaled air passes directly from the air inlet 13 to the air outlet 14 as shown by arrow A. Once the flow of air for entraining droplets B has passed beneath the baffle 9, it returns around the outside of the baffle 9 to rejoin the through flow of air A. A further advantage of this embodiment is that only a certain volume of air passes under the baffle 9 in a given time. The nebulizer works most effectively when the flow of air for entraining droplets is of the rate of about 25 liters per minute. If this rate of flow of air is much greater than this or much less than this, the effectiveness of entrainment decreases. This means that if the patient inhales sharply, the rate of through flow of air A increases without significantly altering the flow of air for entraining droplets B passing beneath the baffle.

I claim:

1. An atomizer comprising:

a head having a gas exit and at least one outlet adjacent said gas exit;

a deflector for deflecting gas issuing from said gas exit over at least one of said outlets, for drawing a substance to be atomized out from at least one of said outlets and atomizing the substance in the gas issuing from said gas exit; and said deflector mounted with respect to said head so that said deflector is movable between a first position in which said deflector is adjacent said gas exit and directly in the path of gas issuing from said gas exit so that atomization of the substance takes place, and a second position spaced from said gas exit so that no atomizing takes place.

2. An atomizer as recited in claim 1 further comprising condition responsive means for automatically moving said deflector between said first and second positions in response to a condition.

3. An atomizer as recited in claim 2 wherein said condition responsive means comprises a vane connected to said deflector and effecting movement of said deflector in response to air pressure conditions acting on said vane.

4. An atomizer as recited in claim 1 wherein said deflector is mounted with respect to said jet head by a pivot, so that said deflector pivots between said first and second positions.

5. An atomizer as recited in claim 1 further comprising a vane for moving said deflector between said first and second positions.

6. An atomizer as recited in claim 5 wherein said deflector comprises a bar connected to said vane.

7. An atomizer as recited in claim 1 further comprising an air inlet and an air outlet providing for the flow of air toward and past said head, said outlet permitting flow of atomized substance to a human.

8. An atomizer as recited in claim 7 wherein said deflector moves into said first position when air flows from said air inlet to said air outlet.

9. An atomizer as recited in claim 7 wherein said deflector moves into said second position when air is not flowing from said air inlet to said air outlet.

10. An atomizer as recited in claim 3 further comprising an air inlet and an air outlet for providing the flow of air to and past said head; and wherein said deflector is biased to said second position and wherein said vane is biased to a position closing said air inlet.

11. An atomizer as recited in claim 10 wherein said vane is positioned to direct a flow of air toward said gas exit when air flows from said air inlet to said air outlet.

12. An atomizer as recited in claim 10 wherein said vane is mounted to allow air flow from said air outlet directly through said air inlet, without passing past said head.

13. An atomizer as recited in claim 10 wherein said vane is mounted so as to allow a proportion of the air flowing from said air inlet to said air outlet to by-pass said head when the air flow rate exceeds a predetermined value.

14. An atomizer as recited in claim 4 wherein said deflector comprises a bar with an arcuate surface.

15. An atomizer as recited in claim 2 wherein said condition is a human inhaling and exhaling during breathing.

16. An atomizer as recited in claim 15 wherein said deflector is positioned so that during exhaling, exhaled air does not entrain the substance to be atomized.

17. An atomizer as recited in claim 1 further comprising a baffle extending outwardly and downwardly about said gas exit; and wherein said deflector is mounted within said baffle and movable with respect to said baffle.

18. An atomizer comprising:

a head having a gas exit and at least one outlet adjacent said gas exit;

a deflector for deflecting gas issuing from said gas exit over at least one of said outlets, for drawing a substance to be atomized out from at least one of said outlets and atomizing the substance in the gas issuing from said gas exit;

said deflector mounted with respect to said head so that said deflector is movable between a first position in the path of gas issuing from said gas exit for atomization, and a second, non-atomizing, position; and a vane for moving said deflector between said first and second positions.

19. An atomizer as recited in claim 18 wherein said deflector is mounted with respect to said head by a pivot, so that said deflector pivots between said first and second positions.

20. An atomizer as recited in claim 18 wherein said vane is integral with said deflector.

21. An atomizer as recited in claim 18 wherein said deflector comprises a surface elongated in a first dimension and having a first width; and wherein said vane comprises a surface elongated in a second dimension substantially perpendicular to said first dimension and has a second width much greater than said first width so that said vane moves, and effects movement of said deflector, in response to breathing action by a human.

22. An atomizer as recited in claim 21 further comprising a baffle extending outwardly and downwardly about said gas exit; and wherein said deflector is mounted within said baffle and movable with respect to said baffle.

23. An atomizer comprising:

a head having a gas exit and at least one outlet adjacent said gas exit;

a deflector for deflecting gas issuing from said gas exit over at least one of said outlets, for drawing a substance to be atomized out from at least one of said outlets and atomizing the substance in the gas issuing from said gas exit; and said deflector pivotally mounted with respect to said head so that said deflector is pivotally movable between a first position in the path of gas issuing from said gas exit for atomization, and a second, non-atomizing, position.

24. An atomizer as recited in claim 23 further comprising a baffle extending outwardly and downwardly about said gas exit; and wherein said deflector is mounted within said baffle and movable with respect to said baffle.

25. Spray forming apparatus comprising:

a housing having an outlet for a spray of atomized substance;

a head mounted within said housing and including a pressurized gas exit, and at least one outlet adjacent said gas exit;

a deflector for deflecting gas issuing from said gas exit over at least one of said outlets, for drawing a substance to be atomized out from at least one of said outlets and atomizing the substance in the gas issuing from said gas exit; and said deflector mounted with respect to said head so that said deflector is movable between a first position in which said deflector is adjacent said gas exit and directly in the path of gas issuing from said gas exit so that atomization of the substance takes place, and the atomized substance is sprayed out of said housing outlet, and a second position in which said deflector is spaced from said gas exit so that no atomized substance is sprayed out of said spray outlet.

* * * * *